United States Patent [19]

Ogden et al.

[11] Patent Number: 5,611,458
[45] Date of Patent: Mar. 18, 1997

[54] LIQUID FLOW MONITORING AND CONTROL SYSTEM

[75] Inventors: John E. Ogden; Kent D. Abrahamson; Peter L. Bryant; Thomas P. Joyce, all of Libertyville; John S. Ziegler, Arlington Heights, all of Ill.

[73] Assignee: Abbott Laboratories, Abbott Park, Ill.

[21] Appl. No.: 435,357

[22] Filed: May 5, 1995

[51] Int. Cl.[6] .................................................. B67B 7/00
[52] U.S. Cl. .......................... 222/1; 222/63; 222/207; 604/250
[58] Field of Search ........................... 222/52, 1, 61, 222/63, 207, 214, 642; 604/246, 249, 250, 256

[56] References Cited

U.S. PATENT DOCUMENTS

| | | | |
|---|---|---|---|
| 4,261,356 | 4/1981 | Turner et al. | 604/250 |
| 5,188,455 | 2/1993 | Hammerstedt | 222/214 X |
| 5,230,445 | 6/1993 | Rusnak et al. | 222/207 |
| 5,551,599 | 9/1996 | Niss | 222/63 |

*Primary Examiner*—Gregory L. Huson
*Attorney, Agent, or Firm*—Brian R. Woodworth

[57] ABSTRACT

A method and apparatus are provided for controlling the dispensing of a primary liquid from a pressurized source of primary liquid. Primary liquid is admitted through an inlet valve to a primary chamber having a primary element which is biased toward an initial position but is movable away from the initial position when subjected to the source pressure of the primary liquid. A sensor determines when the primary element has moved away from an initial position to a predetermined final position, and the inlet valve is closed in response thereto. The difference between the initial and final positions defines a predetermined dispensing volume. An outlet valve is opened to dispense the dispensing volume under the biasing force of the primary element which returns to the initial position. A sensor determines when the primary element has returned to the initial position, and the outlet valve is closed in response thereto.

20 Claims, 8 Drawing Sheets

LIQUID FLOW MONITORING AND CONTROL SYSTEM

TECHNICAL FIELD

This invention relates to a liquid delivery system and is particularly suitable for low flow rate delivery of a liquid drug, or the like, to a patient over a relatively long time period.

BACKGROUND OF THE INVENTION AND TECHNICAL PROBLEMS POSED BY THE PRIOR ART

Conventional techniques have been developed for intravenous or intra-arterial delivery of a liquid to a patient by pumping or other form of pressurized delivery. Low flow rate applications may be accommodated by using a peristaltic pump or syringe pump. Such systems typically include disposable components manufactured from thermoplastic materials. It is difficult to manufacture such components relatively inexpensively and still maintain precise dimensional control of the components. When the components are used in a fluid delivery system for providing liquids at low flow rates (e.g., 0.1–100 ml/hr), the accuracy of the flow rate control may not be sufficiently great to permit the use of such a system in certain applications. Alternatively, relatively expensive manufacturing techniques must be employed to insure relatively close dimensional tolerances which would enable such a system to be operated with a more accurate flow control at low flow rates.

Pressurized container systems for delivering liquid typically employ a precision orifice for flow control. The flow rate is dependent upon, among other things, the source pressure, and that source pressure can change during the delivery process (e.g., the pressure may drop as the supply of the liquid is dispensed). In any event, it is difficult to manufacture such an orifice within tight dimensional tolerances. Typically, with a conventional orifice, the overall accuracy of the rate of delivery lies within a range of 20% to 50%. This obviously limits the applications for such orifice-controlled pressurized delivery systems to the delivery of those liquids, such as some drugs, where the accuracy of the flow rate is not critical.

It would be desirable to provide an improved monitoring and control system for liquid delivery at accurate, low flow rates. Such an improved flow monitoring and control system should preferably accommodate the use of relatively inexpensively manufactured components.

Further, it would be desirable if such an improved system could incorporate permanent control components which can be calibrated by the manufacturer and which can be manufactured at relatively low cost, but with the precision necessary to provide low flow rate control at the desired accuracy.

It would also be advantageous if such an improved system could incorporate a disposable cassette structure for receiving and dispensing the liquid.

Such an improved system should also desirably accommodate relatively small, portable designs that can be used by ambulatory and/or confined patients.

In addition, it would be desirable to provide an improved system that could accommodate the use of improved monitoring and recording capabilities for the current flow rate and the total volume of liquid delivered.

It would also be desirable to provide system controls having an accuracy sufficient to permit the delivery of drugs for use in pain management and other therapies which require long term, accurate delivery (e.g., within about 5% accuracy).

The present invention provides an improved liquid flow monitoring and control system which can accommodate designs having the above-discussed benefits and features.

SUMMARY OF THE INVENTION

In accordance with the present invention, an improved liquid flow monitoring and control system provides an economical, reliable, and accurate way to deliver a predetermined volume of liquid. The improved system can be used in hospital applications to eliminate the inconvenience of large pumps. It can be used with ambulatory and confined patients, and it can be used with pressurized container delivery systems, including delivery systems for pain management drugs requiring relatively accurate delivery.

In accordance with one aspect of the invention, a method is provided for controlling the dispensing of a primary liquid from a pressurized source of the primary liquid. An inlet valve is opened for admitting the primary liquid into a primary chamber. The primary chamber has a movable primary element, and the primary element is moved away from an initial or first position against a biasing force by the source pressure of the primary liquid.

The method includes the step of determining when the primary element has moved to an extended position or predetermined final position, and the inlet valve is closed in response to that determination. The difference between the first position of the primary element and the extended position of the primary element defines a dispensing volume.

An outlet valve in communication with the primary chamber is subsequently opened to dispense at least a portion of the volume of primary liquid under the biasing force of the primary element which moves back toward the first position.

Finally, the method includes the step of determining when the primary element has returned to a selected retracted position (which may be the first position), and the outlet valve is closed in response to that determination.

The present invention includes an apparatus for carrying out the method whereby accurate control is effected over the dispensing of the primary liquid from the pressurized source of the liquid. The apparatus includes a primary chamber and an inlet valve for admitting the primary liquid into the primary chamber. The primary chamber has a primary element which is normally biased toward a first position. In a preferred embodiment, the primary element is a resilient diaphragm which is extensible through a range of extension away from an initial position (corresponding to the first position) when subjected to the source pressure of the primary liquid.

A control means is provided for determining when the primary element has moved away from the initial position to the selected extended position (which, in one form of operation, is a predetermined final position). The inlet valve is closed in response to that determination. The difference between the initial and final positions defines the predetermined dispensing volume.

An outlet valve is provided in communication with the primary chamber and can be opened to dispense the predetermined volume of the primary liquid under the biasing force of the primary element which returns toward the first position or initial position.

Finally, the apparatus includes control means for determining when the primary element has returned to the first position and for closing the outlet valve in response thereto.

In a preferred embodiment, the control means includes a secondary chamber adjacent the primary chamber. The secondary chamber is filled with a secondary, hydraulic fluid. The secondary chamber has a first end defined by a resilient first end diaphragm movable in response to the movable primary element and has a second end defined by a resilient, second end diaphragm. A detectable element in the form of an opaque ball is disposed within the secondary liquid contained in the secondary chamber. The ball is movable between initial and final locations corresponding to the initial and final positions, respectively, of the primary element.

A portion of the secondary chamber is preferably transparent. Initial and final sensors, in the form of photoelectric cell sensors, are located along the transparent portion of the secondary chamber whereby actuating radiation directed to one of the sensors is blocked when the ball is at one of the final or initial locations.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same.

DESCRIPTION OF THE PREFERRED EMBODIMENTS

While this invention is susceptible of embodiment in many different forms, this specification and the accompanying drawings disclose only some specific forms as examples of the invention. The invention is not intended to be limited to the embodiments so described, however. The scope of the invention is pointed out in the appended claims.

Figures illustrating the apparatus of the invention show some mechanical elements that are known and that will be recognized by one skilled in the art. The detailed descriptions of such elements are not necessary to an understanding of the invention, and accordingly, are herein presented only to the degree necessary to facilitate an understanding of the novel features of the present invention.

The apparatus of this invention can be used with certain conventional components the details of which, although not fully illustrated or described, will be apparent to those having skill in the art and an understanding of the necessary functions of such components.

Figure 1:
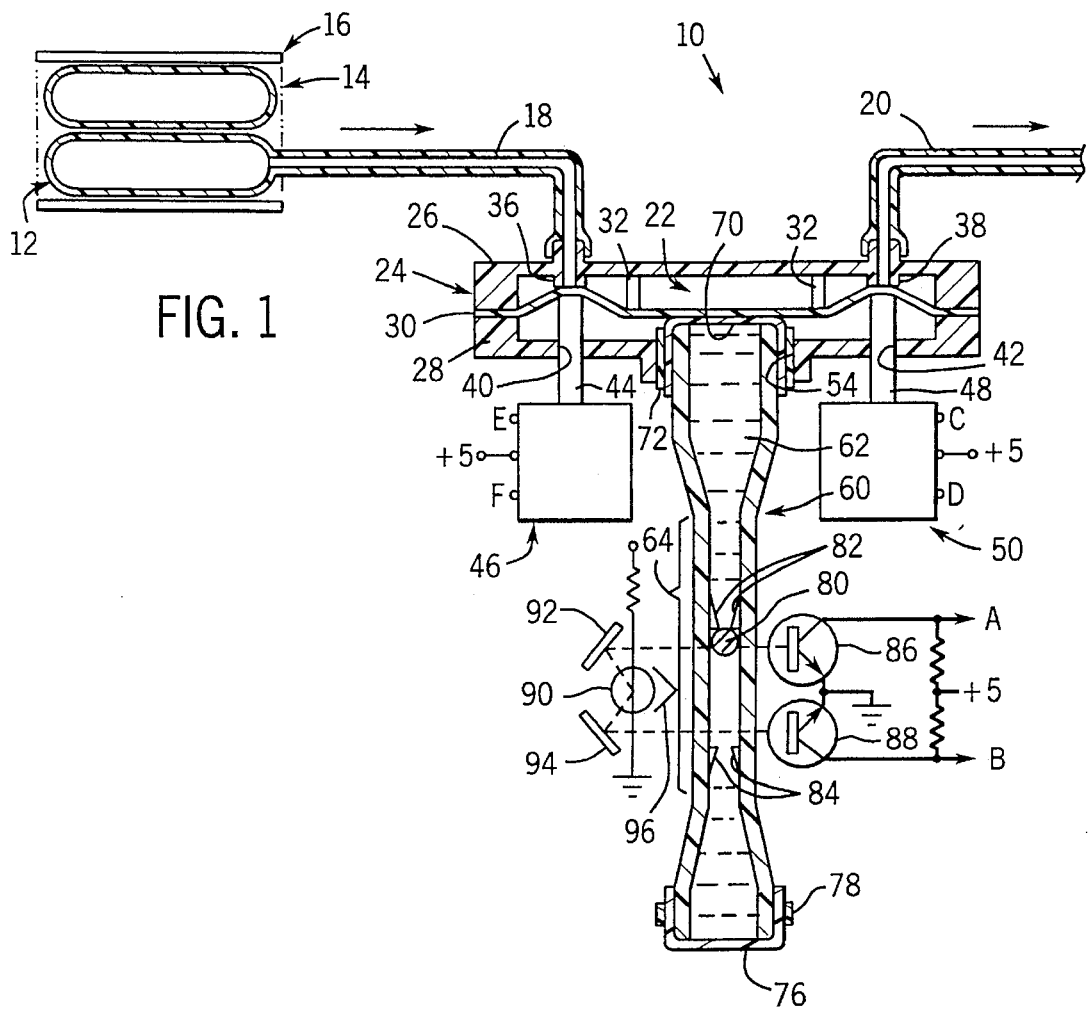
FIG. 1 is a simplified, cross-sectional view, which is partly diagrammatic and partly schematic, showing a first embodiment of the apparatus of the present invention.

With reference to FIG. 1, a first embodiment of the apparatus of the present invention is designated generally therein by the reference number 10. The apparatus 10 is suitable for use in monitoring and controlling the flow of a liquid, such as a liquid drug, from a pressurized container 12. The container 12 may be conventionally pressurized with an auxiliary, pressurizable bladder 14, and both the container 12 and bladder 14 can be conveniently retained in a suitable carrier 16.

The liquid container 12 is connected to the apparatus 10 through suitable inlet tubing 18. The pressurized bladder 14 expands against the container 12, which is flexible, so as to squeeze the liquid out of the container 12 and along the tubing 18. The container 12 and pressurizing bladder 14 may be of any suitable special design or of any conventional design well known to those skilled in the art. The detailed design and operation of the container 12 and bladder 14 form no part of the present invention.

The apparatus 10 is adapted to discharge or dispense a predetermined quantity of liquid. To this end, the apparatus 10 is adapted to be connected to outlet tubing 20 which can be connected to a patient or a selected receiving device.

The apparatus 10 includes a primary chamber 22 defined in a suitable structure or housing which may be in the form of a disposable cassette 24. The cassette 24 includes a primary side housing 26 and a secondary side housing 28 between which a primary diaphragm 30 is clamped in a liquid-tight engagement. The primary diaphragm is resilient, flexible, and extensible.

The primary side housing 26 defines a pair of spacers 32 against which portions of the diaphragm 30 rest. The primary chamber 22 is defined between the diaphragm 30 and the primary side housing 26. The primary side housing 26 has an inlet boss 36 defining an inlet opening communicating between the primary chamber 22 and the inlet tubing 18. The primary housing 26 also has an outlet boss 38 defining an outlet opening communicating between the primary chamber 22 and the outlet tubing 20.

The secondary side housing 28 defines apertures 40 and 42. Aperture 40 receives an actuator rod 44 of an electric transducer such as an electrical solenoid driver 46, and aperture 42 receives an actuator rod 48 of an electrical solenoid driver 50. Preferably, the electrical solenoid drivers 46 and 50 are each of the type that is magnetically latched when de-energized in the extended position illustrated in FIG. 1. Each solenoid driver is actuated by a short-duration pulse of current which energizes the solenoid driver and retracts the actuator rod (to the position illustrated in FIG. 2 for the actuator rod 44 and to the position illustrated in FIG. 4 for the actuator rod 48).

Figure 4:
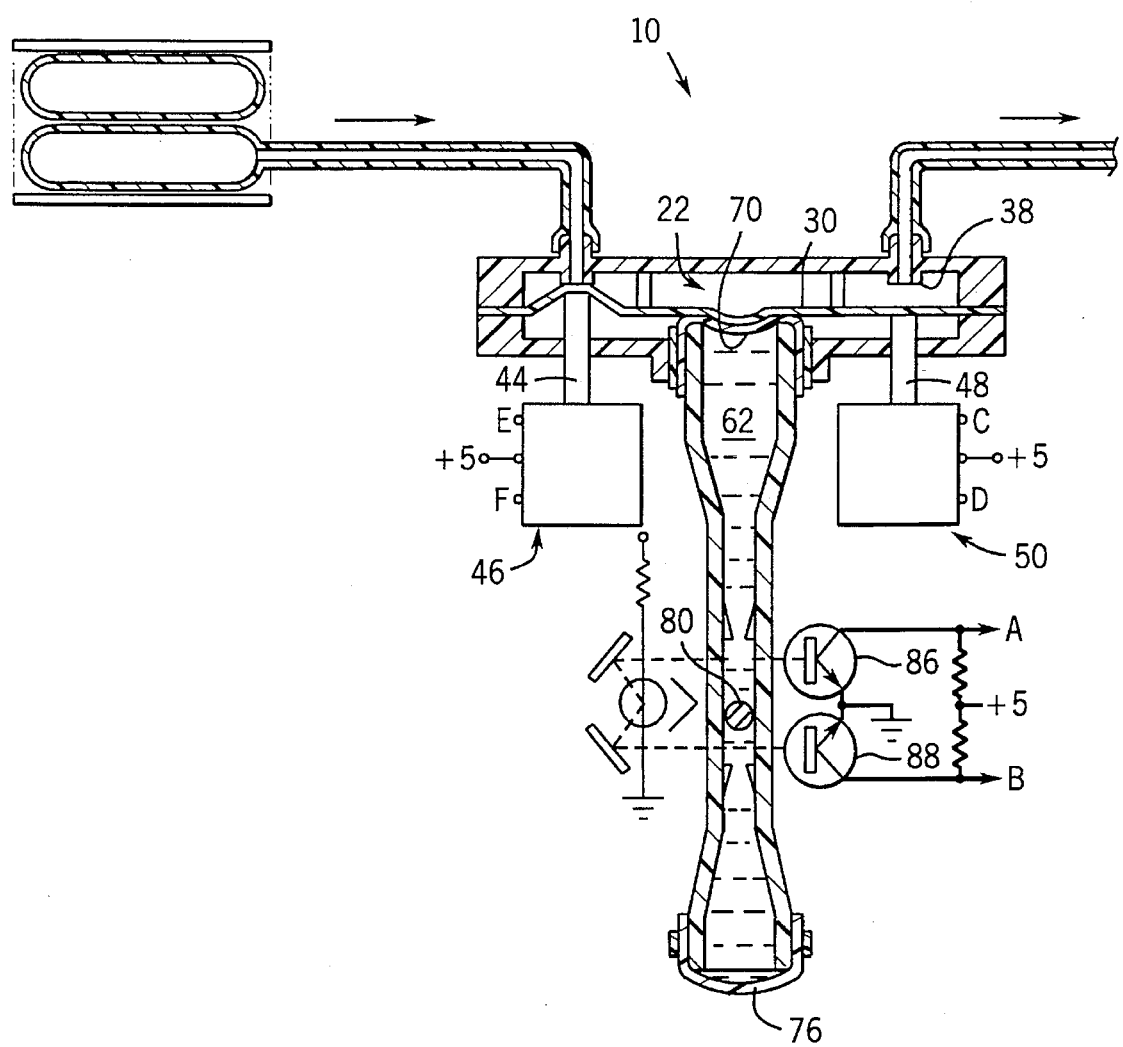

In the de-energized, magnetically latched, extended positions, the actuator rods 44 and 48 bear against the diaphragm 30. A portion of the diaphragm 30 is maintained in a closed relationship against the inlet boss 36 by the actuator rod 44, and a portion of the diaphragm 30 is maintained in a closed relationship against the outlet boss 38 by the actuator rod 48. These portions of the diaphragm, in conjunction with the actuator rods 44 and 48, function as inlet and outlet valves, respectively. When the actuator rods 44 and 48 are retracted during energization of the drivers 46 and 50, respectively, the inherent resiliency of the diaphragm 30 causes the diaphragm portions adjacent the rods 44 and 48 to return to the generally undeflected, straight orientation spaced away from the inlet boss 36 (FIG. 2) and outlet boss 38 (FIG. 4).

The electric solenoid drivers 46 and 50 may be of any suitable special or conventional type. The detailed design of such solenoid drivers forms no part of the present invention.

The secondary side housing 28 of the cassette 24 defines a central aperture 54 for receiving a secondary chamber 60. The secondary chamber 60 contains a suitable hydraulic fluid or secondary fluid 62. The secondary chamber 60 is elongated, and generally cylindrical. In the embodiment illustrated in FIGS. 1–4, the secondary chamber 60 has a reduced diameter central portion 64. The chamber 60 has an enlarged, first end portion with an opening which is occluded at a first end defined by a resilient first end diaphragm 70. The diaphragm 70 is stretched over the first end portion of the chamber 60 and retained thereon by an annular band 72 which is received in the cassette aperture 54.

The secondary chamber 60 has an enlarged, second end portion with an opening occluded at a second end defined by a resilient second end diaphragm 76. The diaphragm 76 is retained on the chamber 60 by an annular band 78.

The diaphragms 70 and 76 are extensible. The chamber 60 is positioned in the cassette 24 so that the first end diaphragm 70 is in face-to-face contact with the central portion of the cassette primary diaphragm 30 when the central portion of the diaphragm 30 is in an undeflected, planar orientation (as shown in FIG. 1). The secondary chamber first end diaphragm 70 may be characterized as being engaged with, or coupled to, the central portion of the cassette diaphragm 30. Movement of the central portion of the diaphragm 30 in the direction toward the secondary chamber first end diaphragm 70 will cause the diaphragm 70 to move in that same direction in response to the movement of the diaphragm 30.

The central, reduced diameter portion 64 of the secondary chamber 60 contains a detectable element which, in the preferred embodiment illustrated, is an opaque ball 80. Preferably, the ball has about the same density as the secondary liquid 62. In a preferred embodiment, the secondary liquid 62 is distilled water which has a viscosity suitable for accommodating movement of the liquid 62 within the secondary chamber 60. When water is employed as the secondary liquid 62, then the ball 80 may be fabricated from polypropylene or polyethylene which has a density sufficiently close to that of water so as to accommodate operation of the system as described in detail hereinafter.

In some applications, the use of water as a secondary liquid 62 may not be preferred because of the general solvent properties of water. It is contemplated that other liquids, such as a low-density silicone oil, may be used where reduced solvent characteristics are desired. The detectable element 80 could then be fabricated from a suitable thermoplastic material having a density about the same as the silicone oil.

If a liquid other than water is employed as the secondary liquid 62, then the viscosity of that liquid should preferably be between about 50% and 150% of the viscosity of water so as to facilitate the movement of the liquid within the secondary chamber at a rate sufficient to accommodate operation of a control system as described in detail hereinafter.

Figure 3:
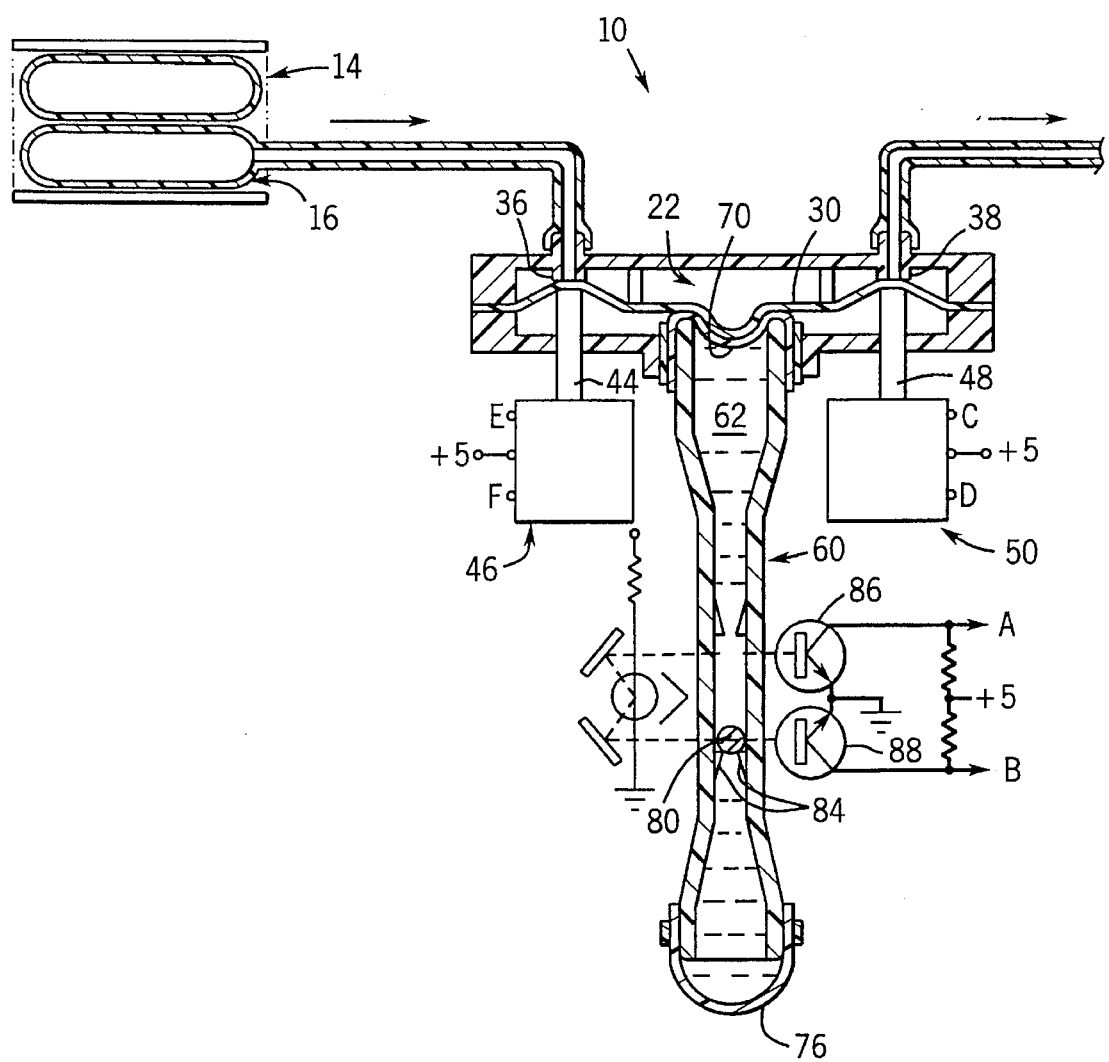

The central portion 64 of the secondary chamber 60 accommodates linear movement of the detectable element or ball 80 from an initial location illustrated in FIG. 1 to a final location illustrated in FIG. 3. In a presently contemplated embodiment, the inside diameter of the secondary chamber central portion 64 is somewhat greater than the diameter of the ball which is about 0.125 inch. There is a very small clearance around the ball 80 adjacent the inside surface of the secondary chamber 60, and this clearance may be between about 0.005 inch and 0.020 inch.

The ball 80 is prevented from moving away from its initial location toward the secondary chamber first end diaphragm 70 by inwardly projecting stop members 82 (FIG. 1). Similarly, as illustrated in FIG. 3, the ball 80 is prevented from moving away from the final location toward the secondary chamber second end by inwardly projecting stop members 84. The stop members 82 and 84 may be separate elements that are secured, as with heat welding or adhesive means, to the inside surface of the secondary chamber 60. Alternatively, the members 82 and 84 may be formed by a mechanical upset of the material in the wall of the secondary chamber 60.

A system is provided for determining when the ball 80 is at the initial location (FIG. 1) and when the ball 80 is at the final location (FIG. 3). In one preferred form of the ball location sensing system, a first photoelectric cell sensor 86 is provided adjacent the initial location, and a second photoelectric cell sensor 88 is provided adjacent the final location. A light source, in the form of a light-emitting diode 90, is located adjacent the secondary chamber 60 between a pair of angled reflectors or mirrors 92 and 94. The mirror 92 reflects the light from the diode 90 to the initial location sensor 86, and the mirror 94 reflects the light from the diode 90 to the final location sensor 88. An opaque shield 96 is provided between the diode 90 and the secondary chamber 60 to prevent light emitted directly from the diode from actuating the photoelectric cell sensors 86 and 88.

The apparatus 10 can be operated to accurately monitor and control the dispensing of primary liquid from the container 12. One exemplary mode of operation will next be described.

Initially, the condition of the apparatus is as shown in FIG. 1. For purposes of this example, it is assumed that the apparatus has previously been primed with primary liquid so that the primary chamber 22 is full of primary liquid. The solenoid drivers 46 and 50 are de-energized and magnetically latched with the actuator rods 44 and 48 in the extended positions illustrated in FIG. I wherein the primary diaphragm 30 is held against the inlet bosses 36 and 38 to prevent flow into and out of the chamber 22.

For purposes of this example, it is also assumed that, owing to prior operation of the apparatus 10 (e.g., during the priming of the system), the detectable element or ball 80 is in the initial location against the stop members 82 as illustrated in FIG. 1. In this location, light emitted from the diode 90 is blocked by the ball 80 so that the photoelectric cell sensor 86 remains unactuated. The initial location of the ball 80 corresponds to, or is representative of, initial, undeflected, first position of the primary diaphragm 30. The photoelectric cell sensor 88 at the ball final location is not initially blocked, and is subjected to light from the diode 90.

When the apparatus is energized, a control system (described hereinafter) permits the apparatus to be started when desired (e.g., via a push-button), and this initially operates the inlet solenoid driver 46 to retract the actuator rod 44 to the position illustrated in FIG. 2. The pressurizing bladder 14 can then operate to force additional liquid from the container 12 into the primary chamber 22 because the portion of the diaphragm 30 adjacent the inlet boss 36 returns, owing to its inherent resiliency, to its undeflected orientation spaced from the inlet boss 36 as illustrated in FIG. 2.

The central portion of the diaphragm 30, owing to its inherent resiliency, exerts a biasing force which tends to act against the pressure force of the primary liquid. However, the pressure force of the liquid is sufficient to overcome the inherent resilient biasing force of the diaphragm 30. This moves the central portion of the diaphragm 30 outwardly—away from the initial or first position—against the secondary chamber first end diaphragm 70.

Figure 2:
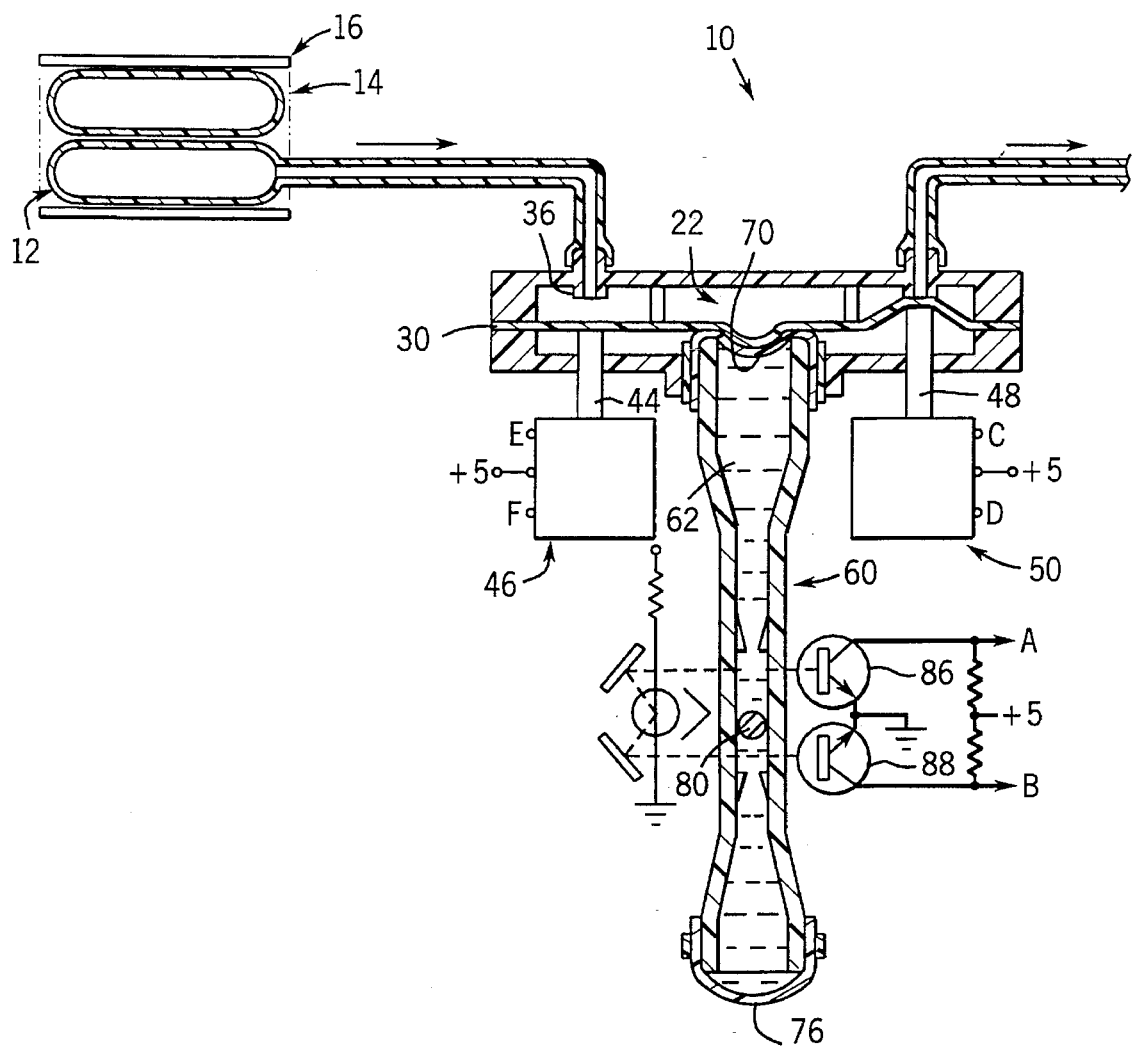
FIGS. 2–4 are views similar to FIG. 1, and FIGS. 2–4 generally illustrate the sequential stages of the operation of the apparatus of the present invention in carrying out one form of the method of the present invention.

As illustrated in FIG. 2, the central portion of the diaphragm 30 and the secondary chamber diaphragm 70 both begin to deflect and stretch inwardly into the adjacent end of the secondary chamber 60. The liquid 62 in the secondary chamber 60 is thus forced toward the secondary chamber second end diaphragm 76, and the diaphragm 76 necessarily bulges outwardly.

As the liquid 62 is moved in the chamber 60 by the first end diaphragm 70, the ball 80 is carried with the liquid 62 away from the initial location at the stop members 82 and toward the stop members 84. Because the ball 80 has substantially the same density as the liquid 62, and because there is substantially no friction between the inside surface of the secondary chamber 60 and the ball 80, the ball 80 is carried with the liquid 62. There is substantially no slip or differential movement between the ball 82 and the adjacent liquid 62. Thus, the location of the ball 80 is a function of the movement of the liquid 62, and the liquid movement is a function of the amount of extension of the diaphragms 30 and 70.

As more primary liquid enters the primary chamber 22, the diaphragms 30 and 70 stretch even further into the end of the secondary chamber 60 toward a selected extended position or final position. Eventually, the ball 80 is carried with the secondary liquid 62 to the final location adjacent the stop members 84 as shown in FIG. 3. At this point, the light directed at the photoelectric cell sensor 88 is blocked by the ball 80, and a signal corresponding to the change of state of the sensor 88 is employed to de-energize the inlet solenoid driver 46. As a result, the inlet solenoid driver 46 returns to its magnetically latched, de-energized state so that the actuator rod 44 again forces the diaphragm 30 against the inlet boss 36. This prevents further primary liquid from entering the primary chamber 22 as illustrated in FIG. 3. As the inlet driver 46 closes, the outlet solenoid driver 50 remains de-energized and magnetically latched so as to maintain the outlet boss 38 closed.

The position of the diaphragm 30 in FIG. 3 is the final position of the diaphragm. The final location of the ball 80 in FIG. 3 corresponds to, or is representative of, the final position of the diaphragm 30.

It will be appreciated that the primary chamber 22 now contains an increased volume of primary liquid. The increased volume of primary liquid is equal to a predetermined dispensing volume of liquid defined by the difference between the initial position of the ball in the tube as shown in FIG. 1, the tube diameter and the final position of the ball in the tube as shown in FIG. 3. The predetermined dispensing volume of primary liquid may be subsequently dispensed when desired by opening the outlet boss 38.

To this end, the control system permits energization of the outlet solenoid driver 50 at any selected time period after the ball 80 has reached its final location (and the inlet solenoid driver 46 has been previously closed). FIG. 4 illustrates the opening of the outlet solenoid driver 50 to permit the predetermined dispensing volume of primary liquid to be dispensed from the primary chamber 22. Owing to the inherent resiliency of the diaphragms 70 and 30, the diaphragms 70 and 30 force the primary liquid out of the primary chamber 22 until the diaphragms return to the undeflected, initial positions (FIG. 1).

As the predetermined dispensing volume of primary liquid is forced by the diaphragms 30 and 70 out of the primary chamber 22 (FIG. 4), the secondary chamber diaphragm 76, owing to its inherent resiliency, necessarily forces the secondary liquid 62 toward the primary chamber 22 until the diaphragm 76 reaches the unextended or undeflected initial position (FIG. 1). As the secondary chamber liquid 62 moves back toward the primary chamber 22, the ball 80 is carried back to the initial location stop members 82 where the light to the initial location photoelectric cell sensor 86 is again blocked. The change of state of the sensor 86 is employed to generate a signal to de-energize the outlet solenoid driver 50. When the outlet solenoid driver 50 is de-energized, it is magnetically latched in the de-energized position with the actuator rod 48 extended so as to force the diaphragm 30 against the primary chamber outlet boss 38, and this insures that the remaining, residual volume of primary liquid in the primary chamber 22 cannot be drawn out of the primary chamber.

It will be appreciated that the above-described operation of the apparatus 10 results in a monitoring and controlling of the dispensing of a precise, predetermined volume of primary liquid. The flow rate can be controlled, if desired, in a variety of ways to provide a relatively accurate system for dispensing the primary liquid. Flow error rates below 1% for a standard deviation are contemplated.

The system may be conveniently employed to administer relatively small volumes of concentrated liquid drugs. This will permit physicians to avoid the conventional practice of dispensing relatively larger volumes of a diluted liquid drug. The reduction of the volume of liquid dispensed to a patient can, in some applications, reduce the likelihood of liver damage that might otherwise occur when large volumes are dispensed to the patient.

A contemplated way to control the rate of flow of the primary liquid with the apparatus 10 will next be described. Initially, the primary chamber 22 is primed and full of primary liquid. The diaphragms 30, 70, and 76 occupy the undeflected positions as illustrated in FIG. 1, and the ball 80 is at the initial location against the stop members 82.

A cycle begins at the end of the previous cycle when the outlet driver 50 was de-energized to close. The new cycle begins with a predetermined first time interval following the end of the previous cycle, and both drivers 46 and 50 are de-energized (closed) during this first time interval.

The inlet driver 46 is opened at the end of the first interval (which may be set as long or short as desired). The inlet driver 46 remains open until the incoming primary fluid has deflected the diaphragms to the point where the ball 80 has reached the final location adjacent the stop members 84 (FIG. 3). As the ball 80 approaches the final location at the stop members 84, the leading surface of the ball begins to intercept the light beam from the reflector 94. The light beam falling on the sensor 88 is not fully blocked instantaneously owing to (a) the width of the sensor 88, (b) the round shape of the ball 80, and (c) the time that it takes the ball to move across the front of the sensor 88.

For the size of the system components presently contemplated in a preferred form of the present invention, wherein the diameter of the ball 80 is about 0.125 inch, the leading surface of the ball approaching the photoelectric cell sensor needs to move only about 0.005 inch from the point at which the ball 80 first starts interrupting the light beam at the edge of the sensor 88 until the sensor 88 is fully blocked and switches state.

In a typical control system contemplated as part of the present invention, the voltage rises from about 0.2 volts to about 4.5 volts as the photoelectric cell sensor changes from being completely unblocked to being completely blocked during the 0.005 inch travel of the ball 80 from the edge of the sensor. The sensing of the final location of the ball by the sensor 88 occurs very rapidly (i.e., during the time period required for the ball to travel the 0.005 inch), and this is insignificant compared to the time that is required for the ball to travel the total path length from the initial location (FIG. 1) into the final location (FIG. 3). The same relationships exist with respect to the initial location sensor 86 during the return movement of the ball 80.

When the final location sensor 88 is actuated by the arrival of the ball 80, the control system de-energizes the inlet solenoid driver 46 to close. Thus, a second time interval is defined between the initial energization of the inlet driver 46 to open and the subsequent de-energization of the inlet driver 46 to close. This second time interval is the "filling" interval. The length of the filling interval time period depends on the length of time required to fill the primary chamber 22 with the predetermined dispensing volume of primary liquid which results in movement of the ball 80 from its initial location (FIG. 1) to its final location (FIG. 3).

Next, the predetermined dispensing volume of primary liquid contained in the primary chamber 22 can be dispensed from the primary chamber 22 after any selected further time interval (i.e., a third time interval) following closure of the inlet solenoid driver 46 (i.e., following the end of the second time interval). In a presently contemplated preferred form of the invention, a suitable, adjustable clock is provided for controlling the third time interval (and first time interval). A signal is generated at the end of the third time interval to energize the outlet driver 50 so as to open the outlet boss 38 and permit the primary liquid to be dispensed.

When the outlet driver 50 is energized to open the end of the third time interval, the predetermined volume of primary liquid is dispensed as previously explained. During the dispensing of the primary liquid, the ball 80 returns to the initial location where it again blocks the sensor 86 to de-energize the outlet driver 50 and close the outlet. The dispensing of the primary liquid, with concomitant ball movement and closure of the outlet driver 50, occurs over a fourth time interval which is necessarily dependent upon the time that it takes for the predetermined dispensing volume of primary liquid to flow out of the apparatus 10 and for the outlet driver 50 to close.

In view of the above discussion, it is seen that the time at which the inlet driver 46 is energized to open, as well as the time at which the outlet driver 50 is energized to open, may be selected as desired. That is, the first time interval (i.e., the time between the previous cycle's closing of the outlet driver 50 and the next cycle's opening of the inlet driver 46) may be predetermined (and hence, adjusted). Likewise, the third time interval (i.e., the time between the closing of the inlet driver 46 and the opening of the outlet driver 50) may be predetermined (and may be adjusted).

The overall flow rate of the primary liquid through the apparatus 10 depends upon the rate at which the apparatus 10 is operated through a complete cycle, and that can be established by controlling (1) the first time interval (from the previous cycle closure of the outlet driver 50 to the next cycle opening of the inlet driver 46, and (2) the third time interval (from the closure of the inlet driver 46 to the opening of the outlet driver 50).

The second time interval (i.e., the filling time defined between the opening and closing of the inlet driver 46) and the fourth time interval (i.e., the dispensing time defined between the opening and closing of the outlet driver 50) depend on system parameters (e.g., primary liquid pressure, system pressure drops, and the predetermined dispensing volume). For a given system, these parameters can be established within a relatively narrow range.

In any event, the second (fill) time interval and fourth (dispensing) time interval are completely determinable (measurable). That is, the second time interval is determined by the length of time that it takes for the ball 80 to move from the initial location (FIG. 1) to the final location (FIG. 3), while the fourth time interval is determined by the length of time that it takes for the ball 80 to move from the final location (FIG. 3) to the initial location (FIG. 1). The system can be designed so that the second and fourth time intervals are a relatively small percentage of the total cycle time. That is, the length of the first and third time intervals, which can be made as short or long as desired, would typically be considerably longer than the second and fourth time intervals.

As a practical matter, the control system can be arranged for a given apparatus design so that the lengths of the second and fourth time intervals are relatively short. A clock control system can be employed to provide a minimum clock pulse interval which is at least greater than either the second time interval (the filling interval) or the fourth time interval (the dispensing interval). This would permit the inlet driver 46 to be energized to open after any selected number of clock pulses because the length of the previous cycle dispensing time interval will necessarily be less than one clock pulse time period. Similarly, the outlet driver 50 could then also be energized to open for dispensing after any selected number of additional clock pulses because the length of the filling time interval will necessarily be less than one clock pulse time period.

Figure 5:
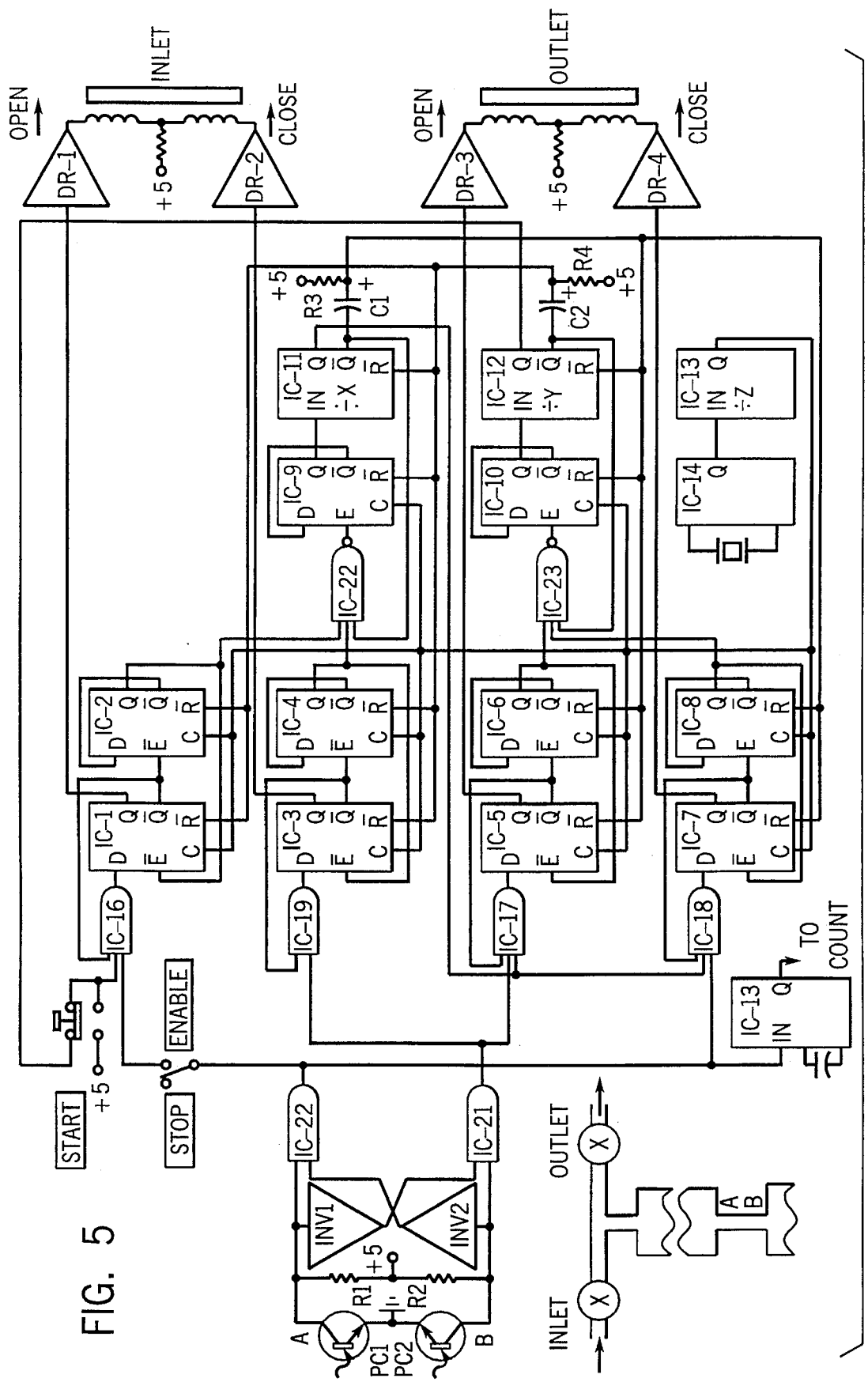
FIG. 5 is a schematic diagram of one example of an electronic circuit that may be employed with the apparatus of the present invention to effect a form of the invention method.

FIG. 5 is a simplified, electrical, schematic diagram of an exemplary electrical control system that may be employed with the apparatus 10. The electrical control system includes a clock which can be adjusted to, in effect, set the rate of actuation of the inlet and outlet drivers 46 and 50.

It will be appreciated that the initial and final locations of the ball 80 could be varied so as to change the predetermined dispensing volume controlled by the apparatus 10. To this end, the stop members 82 and 84 in the secondary chamber 60 could be provided in a manner that would permit them to be adjustable along the length of the chamber. Of course, the associated system for mounting the sensors 88 and 86 would also be correspondingly adjustable. This would accommodate a selection of the extended position, and hence, of the quantity of liquid to be dispensed.

The flow rate through the apparatus 10 may be determined by measuring the elapsed time between the closing of the outlet valve (driver 50) at the end of one cycle and the closing of the outlet valve (driver 50) at the end of the next cycle. The predetermined dispensing volume is then divided by the elapsed time, and the quotient is the flow rate.

It will also be understood that each of the above-described first, second, third, and fourth time intervals can be measured and summed. The sum can be divided by the predetermined dispensing volume, and the quotient will be the flow rate.

The predetermined dispensing volume of primary liquid is, of course, equal to the volume of secondary liquid moved along the secondary chamber 60, and this is equal to the transverse cross-sectional area of the central portion 64 of the chamber 60 multiplied by the distance between the initial ball location (FIG. 1) and final ball location (FIG. 3).

It will also be realized that the number of times that the operating cycle of the apparatus is repeated can be multiplied by the predetermined dispensing volume, and the product will be the total volume of the primary liquid dispensed.

As described above, the inlet driver 46 and the outlet driver 50, together with the diaphragm 30, function as valves. Other suitable valve systems may be employed. In addition, the inlet and outlet valve systems can be completely separate from the primary diaphragm 30. If desired, automatically actuated inlet and outlet valves may be located directly in the inlet and outlet lines exterior of the primary chamber.

Figure 6:
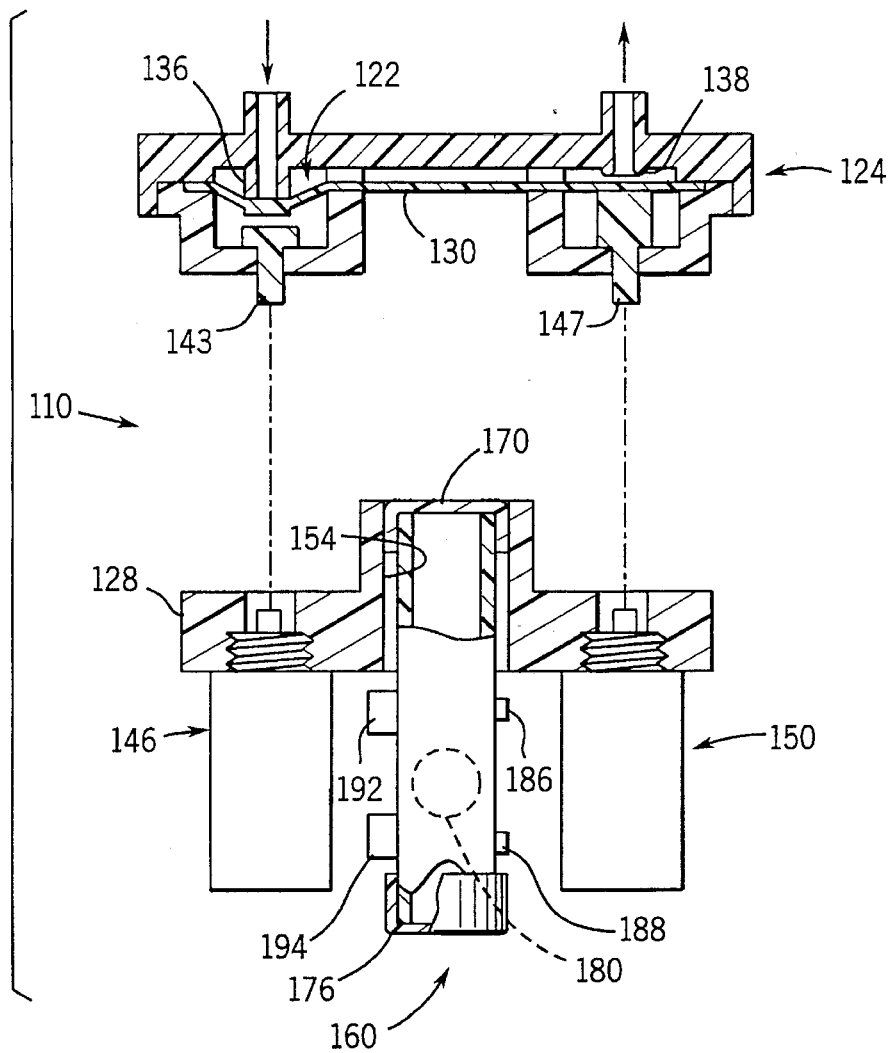
FIG. 6 is a view similar to FIG. 1, but FIG. 6 illustrates a second embodiment of the apparatus of the present invention.
Figure 7:
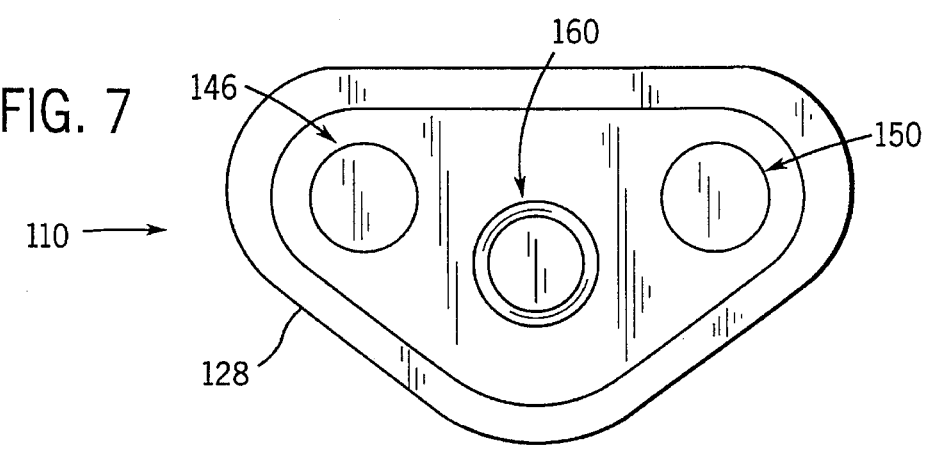
FIG. 7 is a bottom plan view of the apparatus shown in FIG. 6.

A second embodiment of the apparatus of the present invention is illustrated in FIGS. 6 and 7 and is designated generally therein by the reference number 110. The apparatus 110 includes an upper housing 124 containing a diaphragm 130. A primary chamber 122 is defined on one side of the diaphragm 130. The housing defines an inlet boss 136 and an outlet boss 138 adjacent the inside surface of the diaphragm 130. The inlet boss 136 defines an inlet opening through which the primary liquid can flow from a pressurized container (not shown), and the outlet boss 138 defines an outlet opening through which the primary liquid can flow from the primary chamber 122.

The inlet boss 136 extends into the chamber further than does the outlet boss 138. The diaphragm 130, in the undeflected, unpressurized condition, is spaced away from the outlet boss 138, but is stretched over the inwardly protruding inlet boss 136 so as to provide a sealed closure at the inlet.

The upper housing 124 contains an inlet valve drive member 143 for movement between a retracted position (as illustrated in FIG. 6) and a closed position against the diaphragm 130 to maintain the diaphragm 130 tight against the inlet boss 136.

An outlet drive member 147 is retained in the housing 124 adjacent the diaphragm 134. The member 147 is adapted to move between a retracted position illustrated in FIG. 6 and a retracted position pushing the diaphragm tight against the outlet boss 138 to prevent flow of the primary liquid out of the primary chamber 122.

The member 143 is adapted to be connected to an electric solenoid inlet driver 146, and the member 147 is adapted to be connected to an electric solenoid outlet driver 150. The drivers 146 and 150 are carried on a support housing or plate 128. Each driver 146 and 150 may be of the same type as the drivers 46 and 50 described above with reference to the first embodiment illustrated in FIGS. 1–5. Thus, each driver 146 and 150, when de-energized, has a magnetically latched position in which the members 143 and 147 are extended so as to maintain the diaphragm closed 130 against the inlet and outlet bosses 136 and 138. The driver member 143 is shorter than the driver member 147 so as to accommodate the greater inward projection of the inlet boss 136 compared with the outlet boss 138.

The support housing 128 has a central opening 154 for receiving a secondary chamber 160 filled with a secondary, hydraulic liquid. The secondary chamber 160 is substantially similar to the secondary chamber 60 described above with reference to the embodiment illustrated in FIGS. 1–5. In particular, the secondary chamber 160 has a generally cylindrical configuration with an open first end covered by a first end diaphragm 170. When properly assembled for operation, the secondary chamber first end diaphragm 170 is in face-to-face contact with the primary diaphragm 130. The secondary chamber 160 also has an open second end covered by a second end diaphragm 176.

The secondary chamber 160 contains a secondary liquid and a ball 180 which preferably has a density similar to that of the secondary liquid. The ball 180 is adapted to move between an initial location and a final location within the chamber 160. Such locations are defined by suitable stop members (not visible in FIG. 6) which can be similar to the stop members 82 and 84 described above in detail with reference to the first embodiment illustrated in FIG. 1. Similarly, a suitable sensing system is provided for detecting the location of the ball 180, and such a sensing system can include photoelectric cell sensors 186 and 188 responsive to light sources 192 and 194 transmitting through a transparent portion of the secondary chamber 160.

The apparatus 110 can be provided with an electrical control circuit substantially identical with that employed in the first embodiment of the apparatus 10 described above with reference to FIGS. 1–5. The apparatus 110 can be operated in substantially the same manner as previously described for the first embodiment of the apparatus 10.

Figure 8:
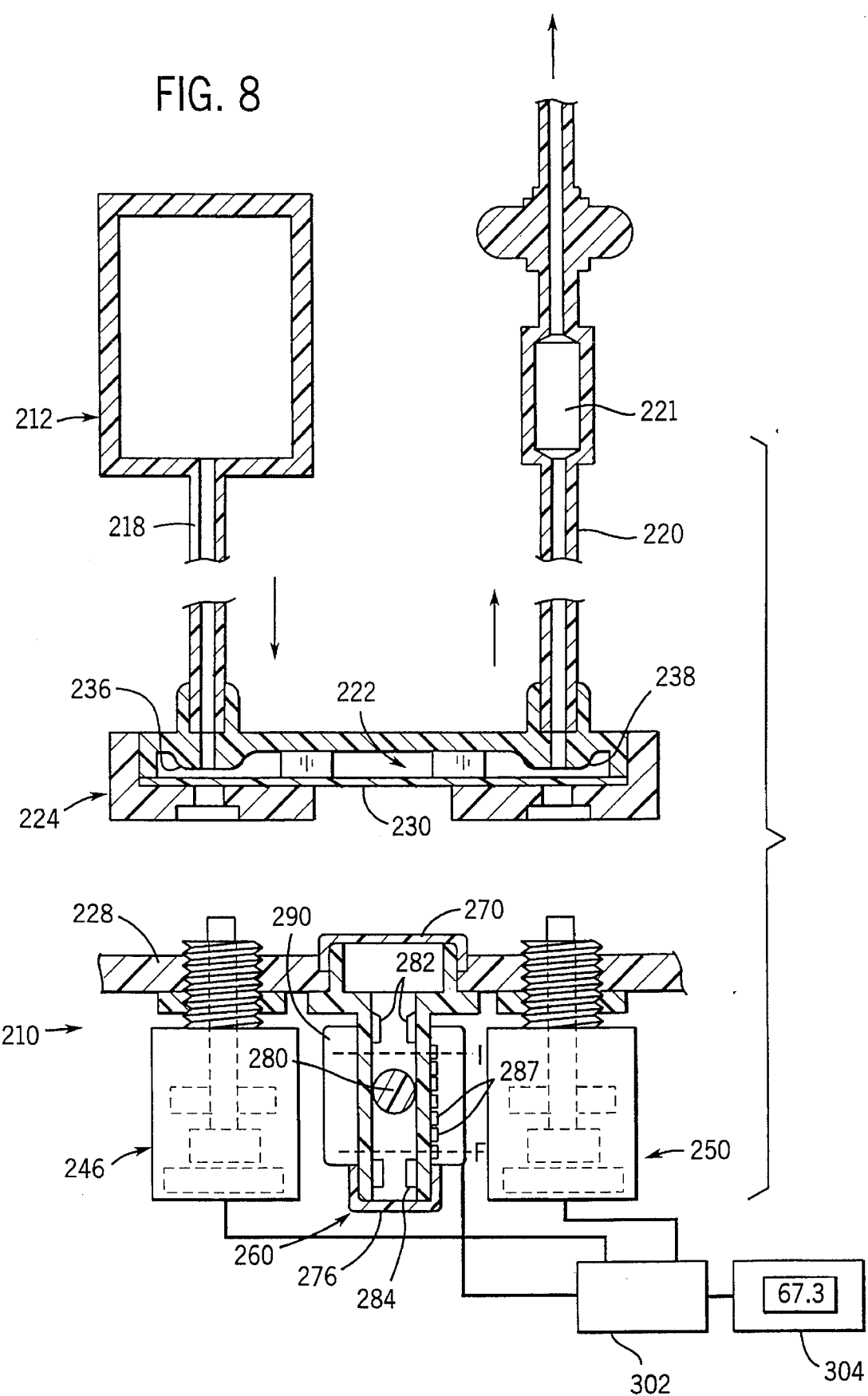
FIG. 8 is a view similar to FIG. 1, but FIG. 8 illustrates a third embodiment of the apparatus.

FIG. 8 illustrates another modified form of the apparatus of the present invention which is designated generally by reference numeral 210 in FIG. 8. The apparatus 210 includes a cassette or housing portion 224 having a primary chamber 222 defined on one side by a resilient diaphragm 230. The housing portion 224 includes an inlet boss 236 defining an inlet opening connected to an inlet conduit 218 that communicates with a pressurized primary liquid container 212. The housing portion 224 defines an outlet boss 238 defining an outlet opening connected to an outlet conduit 220. A suitable filter and flow limiter assembly 221 may be connected in the outlet conduit 220 along with other components that may be desirable in the particular application.

A housing portion or platform 228 contains an electrical solenoid inlet driver 246 and an electrical solenoid outlet driver 250 for each engaging portions of the primary diaphragm 230 adjacent the inlet and outlet bosses, respectively. The platform 228 also carries a secondary chamber 260 having a first end diaphragm 270, a second end diaphragm 276, and a ball 280 which is adapted to move between a first location defined by stop members 282 and a final location defined by stop members 284.

The location of the ball 280 is sensed with a strip assembly of photoelectric cells 287 which are mounted longitudinally along a transparent section of the secondary chamber 260. On the other side of the secondary chamber 260 is a light source 290 which is appropriately collimated for registration with the individual sensors.

The use of a strip photoelectric cell sensor assembly 287 provides a substantially continuous position indication of the ball 280. The output from the sensors can be readily digitalized for use in an appropriate electrical control system.

The continuous photoelectric cell sensor assembly is illustrated in FIG. 8 as being connected with a control system 302 along with the inlet and outlet solenoid drivers 246 and 250. A display panel 304 can be provided with the control system. Of course, if desired, the signals from only the first sensor adjacent the initial location and from the last sensor adjacent the final location need be employed for operation of the apparatus 210 in substantially the same manner as described above with reference to the first and second embodiments illustrated in FIGS. 1–7.

Figure 11:
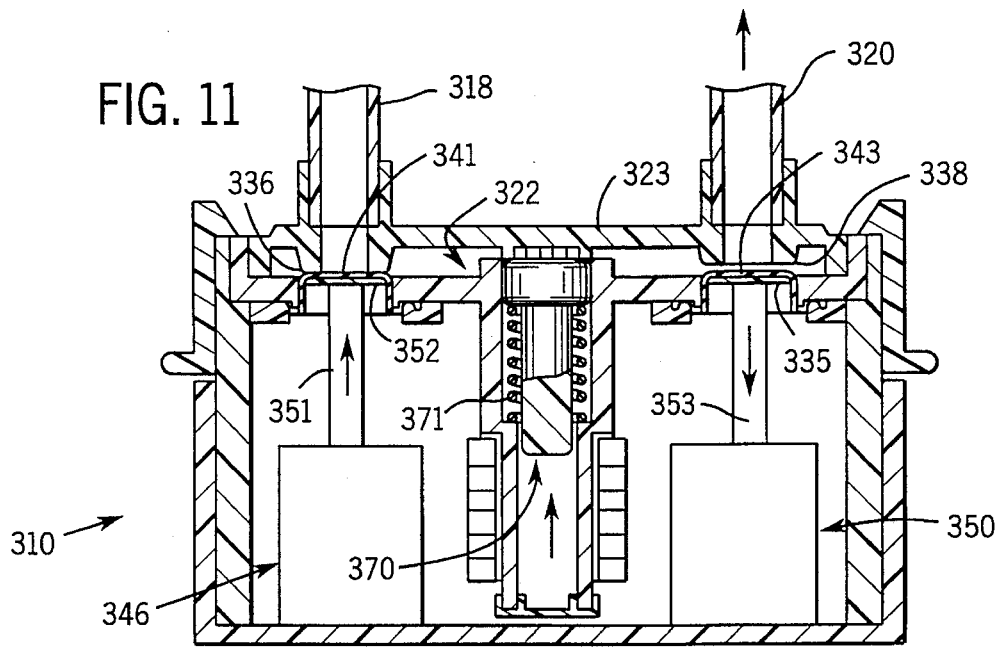
FIG. 11 is a view similar to FIG. 3, but FIG. 11 illustrates the fourth embodiment.
Figure 9:
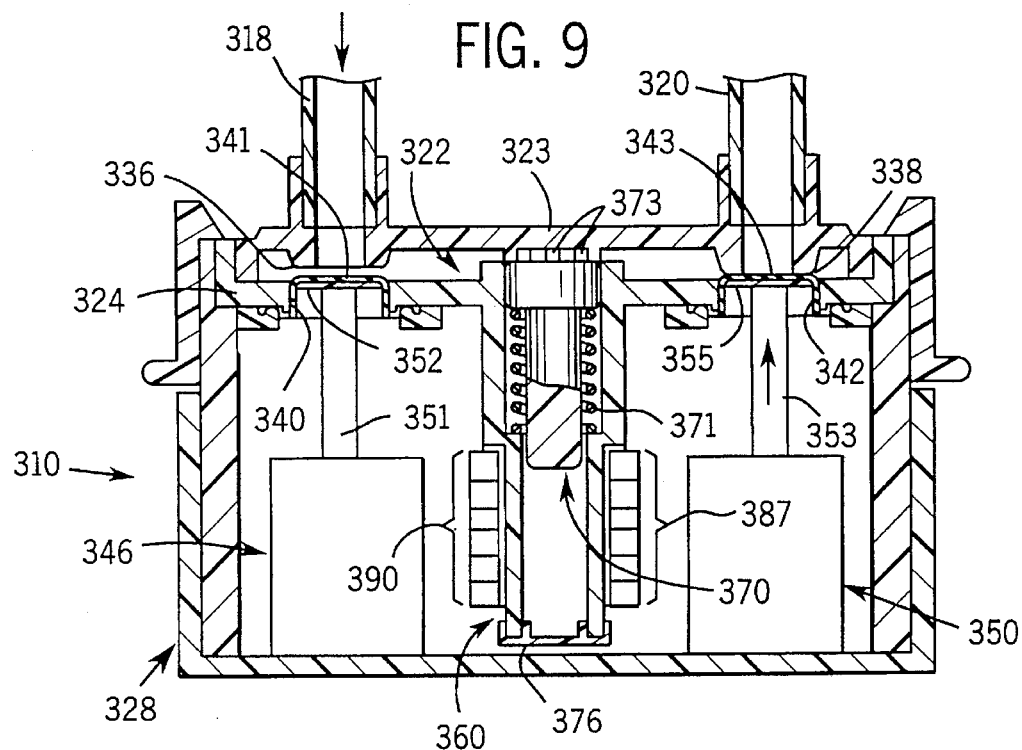
FIGS. 9 and 10 are views similar to FIG. 2, but FIGS. 9 and 10 illustrate a fourth embodiment of the apparatus.
Figure 10:
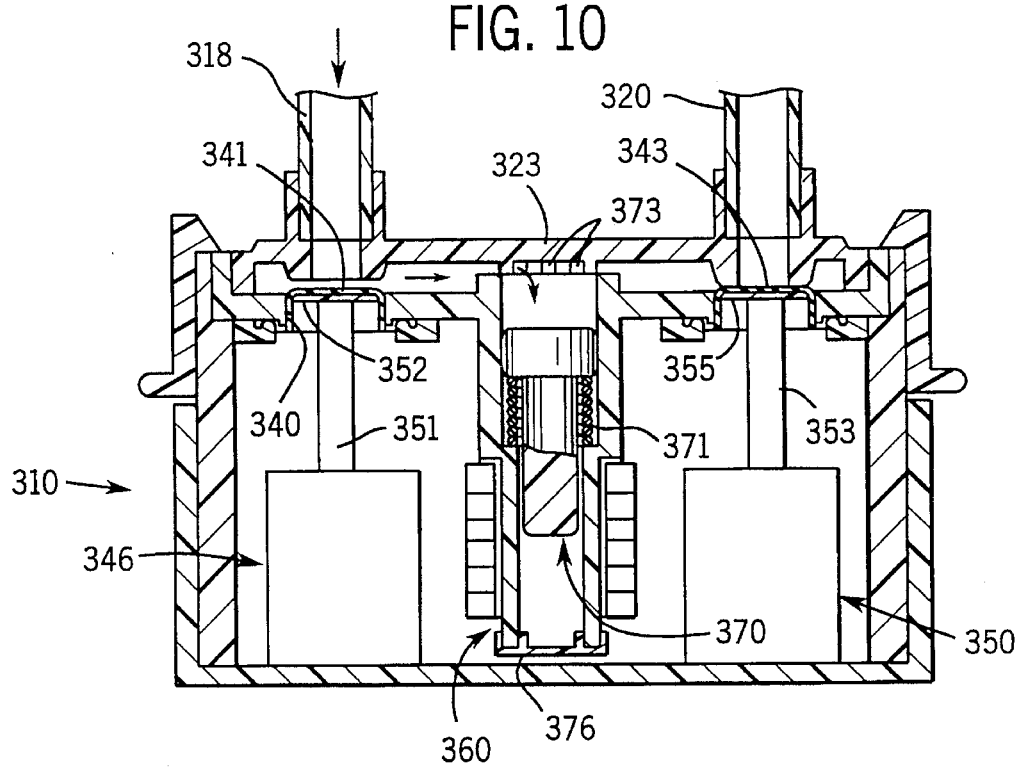

FIGS. 9–11 illustrate a fourth form of the apparatus of the present invention which is designated generally by reference number 310 in FIGS. 9–11. The apparatus 310 includes a front plate 323 and rear plate 324 defining a primary chamber 322. The front plate 323 includes an inlet boss 336 defining an inlet opening connected to an inlet conduit 318 that communicates with a pressurized primary liquid container (not shown). The front plate 323 also defines an outlet boss 338 defining an outlet opening connected to an outlet conduit 320.

The rear plate 324 defines a first bore 340 aligned with the inlet boss 336 and defines a second bore 342 aligned with the outlet boss 338. A first diaphragm 341 is stretched and clamped across the bore 340. Stretched and clamped across the bore 342 is a second diaphragm 343. The diaphragms 341 and 343 are adapted to be moved between (1) stretched positions sealing against the bosses 336 and 338, respectively, to occlude the bores and (2) retracted (less stretched) positions spaced from the bosses.

A housing portion or platform 328 is mounted to the rear plate 324 and contains an electrical solenoid inlet driver 346 and an electrical solenoid outlet driver 350. The inlet driver 346 has an actuating rod 351 with a flat disc 352 at its distal end. The disc 352 is adapted to engage the adjacent surface of the diaphragm 341 in the bore 340. Similarly, the outlet driver 350 has an actuating rod 353. The end of the actuating rod 353 has a disc 355 which engages the adjacent surface of the diaphragm 343 in the bore 342.

Each driver 346 and 350 may be of the same type as the drivers 46 and 50 described above with reference to the first embodiment illustrated in FIGS. 1–5. Thus, each such driver 346 and 350, when de-energized, has a magnetically latched position in which the actuating rods 351 and 353, respectively, are extended. As shown in FIG. 9, when the outlet driver 350 is de-energized, the actuating rod disc 355 forces the diaphragm 343 to seal closed the outlet boss 338.

When the outlet driver 350 is energized, the disc 355 is retracted, and the diaphragm 343 moves away from the outlet boss 342 to permit flow from the chamber 322 through the outlet conduit 320.

Similarly, FIG. 11 illustrates the de-energized condition of the inlet driver 346 wherein the actuating rod disc 352 is maintained in the extended position to hold the diaphragm 341 sealed closed against the inlet boss 336. When the inlet driver 346 is energized, the disc 352 is retracted as shown in FIGS. 9 and 10 so as to permit the primary liquid to flow from the inlet conduit 318 into the primary chamber 322.

The rear plate 324 also carries a secondary housing 360 having a piston 370 at a first end communicating with the primary chamber 322 and having an end cap 376 at a second end. The end cap 376 need not be a diaphragm, and is preferably a rigid cap with a suitable filter and vent system (not illustrated) to permit inflow and outflow of air to accommodate the movement of the piston 370.

The location of the bottom end of the piston 370 is sensed with a strip assembly of photoelectric cell sensors 387 which are mounted longitudinally along a transparent section of the secondary chamber 360. On the other side of the secondary chamber 360 is a light source 390 which is appropriately collimated for registration with the individual sensors.

The use of a strip photoelectric cell sensor assembly provides a substantially continuous position indication of the bottom end of the piston 370. The output from the sensors can be readily digitalized for use in an appropriate electrical control system.

The piston 370 has an area and stroke determinative of a predetermined dispensing volume. The piston 370 is biased by a suitable means, such as a spring 371, to a first position or initial position. In the initial position, the top end of the piston 370 engages a plurality of teeth 373 which extend into the primary chamber 322 from the front plate 323. There are spaces between the teeth 373 to accommodate the flow of primary liquid between the teeth 373 and against the upper end of the piston 370. When sufficient primary liquid has entered the primary chamber 322 to fill the chamber, any additional liquid causes the piston 370 to be pushed downwardly against the spring 371 which is compressed. The piston 370 thus functions in a manner analogous to that of the primary diaphragms 70 and 30 in the first embodiment of the invention described above with reference to FIG. 1.

The location of the bottom end of the piston 370 is sensed by the strip photoelectric cell sensors 387. If desired, an adjustable abutment or fixed abutment (not illustrated) may be provided within the secondary housing 360 to prevent movement of the piston 370 beyond a certain point. This would establish a predetermined dispensing volume of the primary liquid within the system.

Alternatively, a suitable control system may be provided for determining the position of the piston 370 at discrete, small incremental distances along the secondary housing 360 by means of the sensors 387 and by then correlating the piston location at any point to a corresponding volume of primary liquid. The control system could permit the selection of any predetermined volume. When the piston bottom end blocks the particular sensor corresponding to the selected volume, the control system de-energizes the inlet solenoid driver 346 to terminate the flow of primary liquid into the primary chamber 322. Then the outlet solenoid driver 350 can be energized to open the outlet (FIG. 11). The spring 371 then forces the piston 370 back toward the primary chamber 322 to expel the volume of primary liquid through the outlet conduit 320.

In an alternate embodiment (not illustrated), the spring 371 may be mounted on the outside of the secondary housing 360, and the piston 70 may include a portion that extends out through the secondary housing 360 so as to be engaged by the spring. This would permit the spring to be more easily accessed for maintenance or replacement.

The secondary housing 360 in the fourth embodiment illustrated in FIGS. 9–11 does not function to contain a pressurizable, secondary liquid as do the secondary chambers in the embodiments illustrated in FIGS. 1–8. However, the bottom end of the piston 370 in the embodiment illustrated in FIGS. 9–11 does function as a detectable element which is detected by the photoelectric cell or cells in a manner analogous to the detection of the detectable bails (e.g., 80, 180, and 280) in the embodiments described above with reference to FIGS. 1–8.

It will be appreciated that while the path of movement of the detectable element (e.g., balls 80, 180, and 280 described above with reference to the embodiments illustrated in FIGS. 1–8) may be linear, a non-linear path may be employed instead. Indeed, in some applications, it may be preferable to employ a spiral path or other curved path which may provide a longer path within a given length of the apparatus. This may provide a more sensitive control system.

It will also be appreciated that the system of the present invention readily accommodates adjustability and control throughout a continuum of dispensing volumes. The use of a plurality of sensors along the path of the detectable element permits a continuous monitoring of the location of the detectable element, and hence, a continuous monitoring of the amount of primary liquid contained within the system.

Indeed, a strip of sensors along the path of the detectable element can be employed to accommodate errors or variability in a system and to correct the overall dispensing flow rate or dosage by appropriately altering the length of time that the inlet and/or outlet solenoid drivers remain open or closed. For example, when the detectable element reaches a predetermined location as the primary chamber is pressurized, the inlet valve will close in response to actuation of the sensor at the predetermined location. However, if speed of the inlet valve closure is slightly reduced (owing, for example, to mechanical binding or other unforeseen reasons) and more primary liquid enters the primary chamber, then the detectable element will be forced to move further (in the embodiment shown in FIGS. 9-11). However, the further movement and final location will be detected by the sensors. Thus, the corresponding slight increase in volume could be corrected by subsequently opening the outlet driver for a shorter period of time or until the detectable element moved only partway back to a position that would correspond to the smaller volume of primary liquid that was originally selected to be dispensed.

The system of the present invention may also be used to determine if there are occlusions (low flow or no flow rate conditions in the system). For example, if a selected volume cannot be dispensed from the primary chamber, the failure of the detectable element to return to the retracted or initial position will be apparent, and such a condition can be alarmed with a suitable control system.

In a preferred process for controlling the apparatus of the present invention (e.g., apparatus 10, 110, 210, or 310), an electronic clock can be employed as previously described in detail with reference to the first embodiment illustrated in FIGS. 1-5. The use of an electronic clock control system accommodates a variety of beneficial control arrangements. For example, a patient can use the flow control apparatus at home, and the apparatus could then be connected from time-to-time through a modem to a computer in a doctor's office. This would permit the computer to read or calculate the current flow rate and total volume of liquid dispensed.

The doctor would also be able to control the operation of the apparatus from the doctor's office. For example, the computer could be operated to set the apparatus for a different flow rate.

In the preferred forms of the apparatus of the present invention, where magnetically latched solenoid drivers are employed, energy consumption can be kept relatively low because only a pulse current is needed to operate the drivers intermittently. Further, the photoelectric cell sensor circuit and electronic clock pulse counter system may employ complementary metal oxide semiconductor type components for use in low current microcircuits.

The apparatus of the present invention accommodates a variety of designs which can provide relatively high control accuracy with respect to the flow rate. The accuracy of the system is dependent primarily upon the electronic clock, diameter of the secondary chamber, and distance between the initial and final positions of the ball. These aspects of the apparatus would typically be a permanent part of any commercial system and would be factory calibratable. Because conventional electronic clocks are relatively accurate and because the secondary chamber dimensions can be relatively easily controlled with conventional manufacturing techniques, the flow rate can be accurately controlled.

Further, the components in contact with the primary liquid, such as the cassette components defining the primary chamber, need not be manufactured to strict dimensional tolerances and may be relatively low cost and disposable.

It will be readily apparent from the foregoing detailed description of the invention and from the illustrations thereof that numerous variations and modifications may be effected without departing from the true spirit and scope of the novel concepts or principles of this invention.

What is claimed is:

1. A method for controlling the dispensing of a primary liquid from a pressurized source of said primary liquid, said method comprising the steps of:

(A) opening an inlet valve for admitting said primary liquid into a primary chamber having a movable, primary element which is moved away from a first position against a biasing force by the source pressure of said primary liquid;

(B) closing said inlet valve in response to said primary element moving to an extended position away from said first position whereby the difference between the first position and the extended position defines a volume of primary liquid which can be dispensed;

(C) opening an outlet valve communicating with said chamber to dispense at least some of said volume of said primary liquid under the biasing force of said primary element which moves backward to said first position; and (D) determining when said primary element has moved back to a selected retracted position away from said extended position and closing said outlet valve in response thereto.

2. The method in accordance with claim 1 in which said first position of said primary element in step (A) is a retracted, initial position;

said extended position of said primary element in step (B) is a predetermined, final position whereby the difference between said initial position and final position defines a predetermined dispensing volume of said primary liquid;

step (C) includes opening said outlet valve to dispense said predetermined dispensing volume of said primary liquid under the biasing force of said primary element which returns to said initial position; and step (D) includes determining when said primary element has returned to said initial position and then closing said outlet valve in response thereto.

3. The method in accordance with claim 2 in which step (A) includes providing said primary element in the form of a resilient, primary diaphragm which is extensible through a range of extension away from said first position, and permitting the extension of said diaphragm; and step (B) includes (i) providing a detectable element movable along a path in response to the amount of extension of said primary diaphragm, and (ii) providing a final sensor at a selected final location along said path which corresponds to said predetermined final position of said primary element, and sensing the position of said detectable element in said path at said selected final location which determines that said primary element has moved to said predetermined final position in said primary chamber.

4. The method in accordance with claim 3 in which step (D) includes: providing an initial sensor at a selected initial location along said path which corresponds to said predetermined initial position of said primary element, and sensing the position of said detectable element in said path at said selected initial location which determines that said primary element has returned to said initial position in said primary chamber.

5. The method in accordance with claim 4 in which said detectable element has the form of an opaque ball disposed in a secondary liquid contained in a secondary chamber that has a first end defined by a resilient first end diaphragm coupled to said primary diaphragm and that has a second end defined by a resilient second end diaphragm; and steps (B) and (D) include providing each said final sensor and said initial sensor, respectively, in the form of a photoelectric cell along a transparent portion of said secondary chamber whereby actuating radiation directed to one of said photoelectric cells is blocked when said ball is at one of said final or initial positions.

6. The method in accordance with claim 2 further including the steps of:

repeating steps (A)–(D);

measuring the elapsed time between the termination of an initial step (D) and the termination of the next subsequent step (D); and dividing said predetermined dispensing volume by said elapsed time whereby the quotient is the flow rate.

7. The method in accordance with claim 2 further including the steps of:

repeating steps (A)–(D);

counting the total number of times said steps (A)–(D) are repeated during a selected time interval; and multiplying said total number by said dispensing volume whereby the product is the total volume of said primary liquid dispensed during said selected time interval.

8. The method in accordance with claim 2 further including the steps of:

repeating steps (A)–(D) wherein,
  in step (A), said inlet valve is opened after a predetermined first time interval following the termination of immediately preceding step (D);
  a second time interval is defined between the opening and closing of said inlet valve;
  in step (C), said outlet valve is opened after a predetermined third time interval following said second time interval; and
  a fourth time interval is defined between the opening and closing of said outlet valve;

summing said first through fourth time intervals; and dividing said predetermined dispensing volume by the sum of said first through fourth time intervals whereby the quotient is the flow rate.

9. The method in accordance with claim 1 in which the following steps are included:

providing a secondary liquid in a closed secondary chamber that includes:
  (i) a first end that is movable and coupled to said primary element for pressurizing said secondary liquid in response to the movement of said primary element away from said first position;
  (ii) a second end having a movable secondary element that is in contact with said secondary liquid and is maintained in an initial position by a biasing force which is overcome when the said secondary liquid is pressurized by said primary element whereby said secondary liquid moves within said secondary chamber toward said second end, and whereby said secondary liquid moves back toward said first end when said primary element moves back toward its first position; and
  (iii) a detectable element disposed within said secondary chamber and guided for movement along a path in said secondary chamber in response to movement of said secondary liquid; and providing sensors along said secondary chamber for sensing the position of said detectable element in said secondary chamber at positions corresponding at least to said primary element first position and selected extended position; and in which step (B) includes sensing the position of said detectable element with one of said sensors; and step (D) includes sensing the position of said detectable element with another of said sensors.

10. The method in accordance with claim 1 in which step (D) includes choosing a selected retracted position that is different from said first position whereby only a portion of said dispensing volume is dispensed so as to accommodate variability in the prior steps.

11. A method for controlling the dispensing of a primary liquid from a pressurized source of said primary liquid, said method comprising the steps of:

(A) opening an inlet valve for admitting said primary liquid into a primary chamber having a movable, primary element which is moved away from an initial position against a biasing force by the source pressure of said primary liquid;

(B) determining when said primary element has moved to a predetermined final position and closing said inlet valve in response thereto whereby the difference between the initial and final positions defines a predetermined dispensing volume;

(C) opening an outlet valve communicating with said chamber to dispense said dispensing volume of said primary liquid under the biasing force of said primary element which returns to said initial position; and (D) determining when said primary element has returned to said initial position and closing said outlet valve in response thereto.

12. A method for controlling the dispensing of a primary liquid from a pressurized source of said primary liquid, said method comprising the steps of:

(A) after a predetermined first time interval, opening an inlet valve for admitting said primary liquid into a primary chamber having a movable, primary element that is in contact with said liquid and is maintained in an initial position by a biasing force which is overcome by the source pressure of said primary liquid to move said primary element to a predetermined final position whereby the difference between the initial and final positions defines a predetermined dispensing volume;

(B) determining when said primary element has moved to said final position and closing said inlet valve in response thereto whereby a second time interval is defined between the opening and closing of said inlet valve;

(C) after a predetermined third time interval following said second time interval, opening an outlet valve communicating with said chamber to dispense said dispensing volume of said primary liquid under the biasing force of said primary element which returns to said initial position; and (D) determining when said primary element has returned to said initial position and closing said outlet valve in response thereto whereby a fourth time interval is defined between the opening and closing of said outlet valve.

13. The method in accordance with claim 12 further including the steps of:

measuring said second and fourth time intervals and adding them to said first and third predetermined time intervals to define a full cycle time interval; and dividing said predetermined dispensing volume by said full cycle time interval and displaying the quotient as the flow rate.

14. The method in accordance with claim 12 further including the steps of:

establishing a cumulative count of the number of closings of said outlet valve during a selected time interval; and multiplying said cumulative count by said dispensing volume whereby the product is the total volume of said primary liquid dispensed during said selected time interval.

15. The method in accordance with claim 12 in which the following steps are included:

providing a secondary liquid in a closed secondary chamber that includes (i) a first end that is movable and coupled to said primary element for pressurizing said secondary liquid in response to the movement of said primary element away from said initial position;

(ii) a second end having a movable secondary element that is in contact with said secondary liquid and is maintained in an initial position by a biasing force which is overcome when the said secondary liquid is pressurized by said primary element whereby said secondary liquid moves within said secondary chamber toward said second end, and whereby said secondary liquid moves back toward said first end when said primary element moves back toward its initial position; and (iii) a detectable element disposed within said secondary chamber and guided for movement along a path in said secondary chamber in response to movement of said secondary liquid; and providing sensors along said secondary chamber for sensing the position of said detectable element in said secondary chamber at positions corresponding at least to said primary element initial and final positions; and in which step (B) includes sensing the position of said detectable element with one of said sensors; and step (D) includes sensing the position of said detectable element with another of said sensors.

16. Apparatus for controlling the dispensing of a primary liquid from a pressurized source of said primary liquid, said apparatus comprising:

a primary chamber and an inlet valve for admitting said primary liquid into said primary chamber, said primary chamber having a primary element which is biased toward a first position but is movable away from said first position when subjected to the source pressure of said primary liquid;

control means for determining when said primary element has moved away from said first position to an extended position and closing said inlet valve in response thereto whereby the difference between the first position and the extended position defines a volume of primary liquid which can be dispensed;

an outlet valve communicating with said primary chamber and openable to dispense at least some of said volume of said primary liquid under the biasing force of said primary element which moves back toward said first position; and control means for determining when said primary element has returned to a selected retracted position and closing said outlet valve in response thereto.

17. The apparatus in accordance with claim 16 in which said primary element is in the form of a resilient, primary diaphragm which is extensible through a range of extension between an initial position and a predetermined final position, said initial position and said final position corresponding to said first position and said extended position, respectively;

said selected retracted position corresponds to said initial position; and said control means includes (i) a detectable element movable along a path in response to the amount of extension of said primary diaphragm, and (ii) a final sensor at a selected final location along said path which corresponds to said predetermined final position of said primary element for sensing the position of said detectable element in said path at said selected final location which determines that said primary element has moved to said predetermined final position in said primary chamber.

18. The apparatus in accordance with claim 17 in which said control means includes an initial sensor at a selected initial location along said path which corresponds to said initial position of said primary element for sensing the position of said detectable element in said path at said selected initial location which determines that said primary element has returned to said initial position in said primary chamber.

19. The apparatus in accordance with claim 18 in which said control means includes a secondary chamber having a transparent portion, said secondary chamber also having (1) a first end defined by a resilient first end diaphragm coupled to said primary diaphragm and (2) a second end defined by a resilient second end diaphragm;

said detectable element has the form of an opaque ball disposed in a secondary liquid contained in said transparent portion of said secondary chamber; and each said final sensor and said initial sensor include a photoelectric cell along said transparent portion of said secondary chamber whereby actuating radiation directed to one of said photoelectric cells is blocked when said ball is at one of said final or initial locations.

20. The apparatus in accordance with claim 17 in which said detectable element path is linear.

* * * * *